United States Patent
Bornhoft et al.

(10) Patent No.: US 12,257,398 B2
(45) Date of Patent: Mar. 25, 2025

(54) MEDICAL DEVICE WITH ANTI-ROTATION PUSH TAB

(71) Applicant: Becton, Dickinson and Company, Franklin Lakes, NJ (US)

(72) Inventors: Stephen Bornhoft, Sandy, UT (US); Marty Stout, South Jordan, UT (US); Carl Ellis, Salt Lake City, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 72 days.

(21) Appl. No.: 18/085,215

(22) Filed: Dec. 20, 2022

(65) Prior Publication Data

US 2023/0118470 A1    Apr. 20, 2023

Related U.S. Application Data

(63) Continuation of application No. 16/920,003, filed on Jul. 2, 2020, now Pat. No. 11,559,660, which is a continuation of application No. 15/467,929, filed on Mar. 23, 2017, now Pat. No. 10,737,059.

(60) Provisional application No. 62/323,525, filed on Apr. 15, 2016.

(51) Int. Cl.
| A61M 25/00 | (2006.01) |
| A61M 25/06 | (2006.01) |
| A61M 39/10 | (2006.01) |

(52) U.S. Cl.
CPC .... *A61M 25/0097* (2013.01); *A61M 25/0606* (2013.01); *A61M 2039/1033* (2013.01)

(58) Field of Classification Search
CPC .......... A61M 25/0097; A61M 25/0625; A61M 2005/1585; A61M 25/0618
See application file for complete search history.

(56) References Cited

U.S. PATENT DOCUMENTS

| 4,191,186 A | 3/1980 | Keeler |
| 4,365,630 A | 12/1982 | McFarlane |
| 4,828,549 A | 5/1989 | Kvalo |
| 4,863,432 A | 9/1989 | Kvalo |
| 4,964,854 A | 10/1990 | Luther |
| 4,973,313 A | 11/1990 | Katsaros et al. |
| 5,018,374 A | 5/1991 | Montano |
| 5,053,014 A | 10/1991 | Van Heugten |
| 5,215,528 A | 6/1993 | Purdy et al. |
| 5,501,675 A | 3/1996 | Erskine |
| 5,676,656 A | 10/1997 | Brimhall |
| 5,700,250 A | 12/1997 | Erskine |

(Continued)

FOREIGN PATENT DOCUMENTS

| CN | 207168789 U | 4/2018 |
| EP | 0747087 A2 | 12/1996 |

(Continued)

*Primary Examiner* — Bradley J Osinski
(74) *Attorney, Agent, or Firm* — Dickinson Wright, PLLC

(57) ABSTRACT

A medical device, comprising a hub or housing having a push tab including a main portion extending radially from an upper surface of the hub or housing, and at least one anti-rotation feature for resisting rotation of the hub or housing. A cannula is directly or indirectly connected to the hub or housing. The medical device may be a catheter, the cannula may be a catheter tube, and the hub or housing may be a catheter hub or an introducer needle tip shield for the catheter.

14 Claims, 9 Drawing Sheets

(56) References Cited

U.S. PATENT DOCUMENTS

| | | | |
|---|---|---|---|
| 5,713,876 | A | 2/1998 | Bogert et al. |
| 5,913,846 | A | 6/1999 | Szabo |
| 5,951,515 | A | 9/1999 | Osterlind |
| 5,954,698 | A | 9/1999 | Pike |
| 5,967,490 | A | 10/1999 | Pike |
| 6,004,294 | A | 12/1999 | Brimhall et al. |
| 6,638,252 | B2 | 10/2003 | Moulton et al. |
| 6,749,588 | B1 | 6/2004 | Howell et al. |
| 6,953,448 | B2 | 10/2005 | Moulton et al. |
| 7,530,965 | B2 | 5/2009 | Villa et al. |
| 7,722,569 | B2 | 5/2010 | Soderholm et al. |
| 7,854,723 | B2 | 12/2010 | Hwang et al. |
| 8,206,355 | B2 | 6/2012 | Thorne |
| 8,216,188 | B2 | 7/2012 | Millerd et al. |
| 8,747,361 | B2 | 6/2014 | Millerd et al. |
| D713,522 | S | 9/2014 | Woehr et al. |
| 9,056,188 | B2 | 6/2015 | Hager et al. |
| 9,095,679 | B2 | 8/2015 | Nishimura et al. |
| 9,456,775 | B2 | 10/2016 | Millerd |
| D819,802 | S | 6/2018 | Burkholz et al. |
| D835,262 | S | 12/2018 | Burkholz et al. |
| D837,368 | S | 1/2019 | Burkholz et al. |
| 10,737,059 | B2 | 8/2020 | Bornhoft et al. |
| 2002/0177812 | A1 | 11/2002 | Moulton et al. |
| 2003/0060760 | A1 | 3/2003 | Botich |
| 2004/0158207 | A1 | 8/2004 | Hunn et al. |
| 2004/0260235 | A1 | 12/2004 | Douglas |
| 2004/0267204 | A1 | 12/2004 | Brustowicz |
| 2006/0229563 | A1 | 10/2006 | O'Reagan et al. |
| 2006/0270991 | A1 * | 11/2006 | Adams ............. A61M 25/0618 604/164.08 |
| 2007/0185441 | A1 | 8/2007 | Fangrow et al. |
| 2007/0191776 | A1 | 8/2007 | Bialecki et al. |
| 2008/0140011 | A1 | 6/2008 | Hager et al. |
| 2009/0105689 | A1 | 4/2009 | Mitchum |
| 2010/0106092 | A1 | 4/2010 | Tanabe et al. |
| 2010/0168674 | A1 | 7/2010 | Shaw et al. |
| 2010/0249713 | A1 | 9/2010 | Burkholz |
| 2011/0054403 | A1 | 3/2011 | Tanabe et al. |
| 2013/0023826 | A1 | 1/2013 | Ishida |
| 2013/0053791 | A1 | 2/2013 | Clark |
| 2014/0025044 | A1 | 1/2014 | Zamarripa et al. |
| 2014/0303561 | A1 | 10/2014 | Li |
| 2014/0364809 | A1 | 12/2014 | Isaacson et al. |
| 2015/0174319 | A1 | 6/2015 | Rieck |
| 2015/0238733 | A1 | 8/2015 | bin Abdulla |
| 2017/0120009 | A1 | 5/2017 | Garrison et al. |
| 2017/0203082 | A1 * | 7/2017 | Foy ................... A61M 25/1002 |

FOREIGN PATENT DOCUMENTS

| | | |
|---|---|---|
| JP | H05345032 A | 12/1993 |
| JP | 2004524926 A | 8/2004 |
| JP | 2005080962 A | 3/2005 |
| JP | 2009-538188 A | 11/2009 |
| JP | 2013-529111 A | 7/2013 |
| JP | 2019-511313 A | 4/2019 |
| WO | 2011118643 A1 | 7/2013 |
| WO | 2013137348 A1 | 9/2013 |
| WO | 2015161299 A1 | 10/2015 |
| WO | 2017074685 A2 | 5/2017 |

\* cited by examiner

MEDICAL DEVICE WITH ANTI-ROTATION PUSH TAB

CROSS-REFERENCE TO RELATED APPLICATION

This application is a continuation of U.S. Nonprovisional application Ser. No. 16/920,003, filed on Jul. 2, 2020, which is a continuation of U.S. Nonprovisional application Ser. No. 15/467,929, filed on Mar. 23, 2017, which claims the benefit under 35 U.S.C. § 119(e) of U.S. Provisional Patent Application Ser. 62/323,525, filed on Apr. 15, 2016. Each of these applications is hereby incorporated by reference in its entireties.

FIELD OF THE INVENTION

The present invention relates, in general, to an anti-rotation push tab for a medical device. More specifically, the anti-rotation push tab is especially adapted for use with intravenous catheters, as well as catheter introducers and guidewire introducers.

BACKGROUND OF THE INVENTION

An intravenous (IV) catheter is typically mounted over an introducer needle having a sharp distal tip in order to properly insert an IV catheter into a patient. At least the distal portion of the catheter tightly engages the outer surface of the needle to facilitate insertion of the catheter into the blood vessel. The distal tip of the needle preferably extends beyond the distal tip of the catheter.

Although typical IV catheter and introducer needle assemblies generally perform their functions satisfactorily, they do have certain drawbacks. Some PIVCs have issues with stability of the catheter hub when advancing it and are prone to free spinning on the insertion needle during the insertion process. Oftentimes, the catheter hub includes a push tab to aid in advancing the catheter hub. As the catheter hub advances, in some cases, it experiences rolling where the catheter hub spins along the axis of the insertion needle. This can cause a problem when the push tab rotates out of reach of the finger being used to advance the catheter hub.

In some cases an edge is provided on the catheter hub so that the user can advance the catheter hub regardless of its angular position. There is a concern in that the edge becomes quite uncomfortable to a patient when the catheter hub has been taped down at the insertion site thus forcing the edge against the patient's soft tissue.

SUMMARY OF EMBODIMENTS OF THE INVENTION

Accordingly, it is an aspect of the present invention to provide features that oppose the rotational movement of a medical device in relation to the user's finger. In the case of an IV catheter, this can enhance the stability of the catheter during insertion, hooding, and threading. Embodiments of the present invention provide a platform that pushes on the user's finger when the catheter begins to rotate and allows the user's finger to resist the rotation and also steer the catheter back to the neutral starting position. Free spinning of the catheter hub can be prevented without making any other design compromises or increasing the cost of the design.

The foregoing and/or other aspects of the present invention are achieved by a medical device, comprising a hub or housing having a push tab including a main portion extending radially from an upper surface of the hub or housing, and at least one anti-rotation feature for resisting rotation of the hub or housing. A cannula is directly or indirectly connected to the hub or housing. The medical device may be a catheter, the cannula may be a catheter tube, and the hub or housing may be a catheter hub or an introducer needle tip shield for the catheter.

The foregoing and/or other aspects of the present invention are also achieved by a medical device, comprising a housing having a push tab including a main portion extending radially from an upper surface of the housing, and at least one anti-rotation feature for resisting rotation of the housing, and a cannula connected to the housing.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
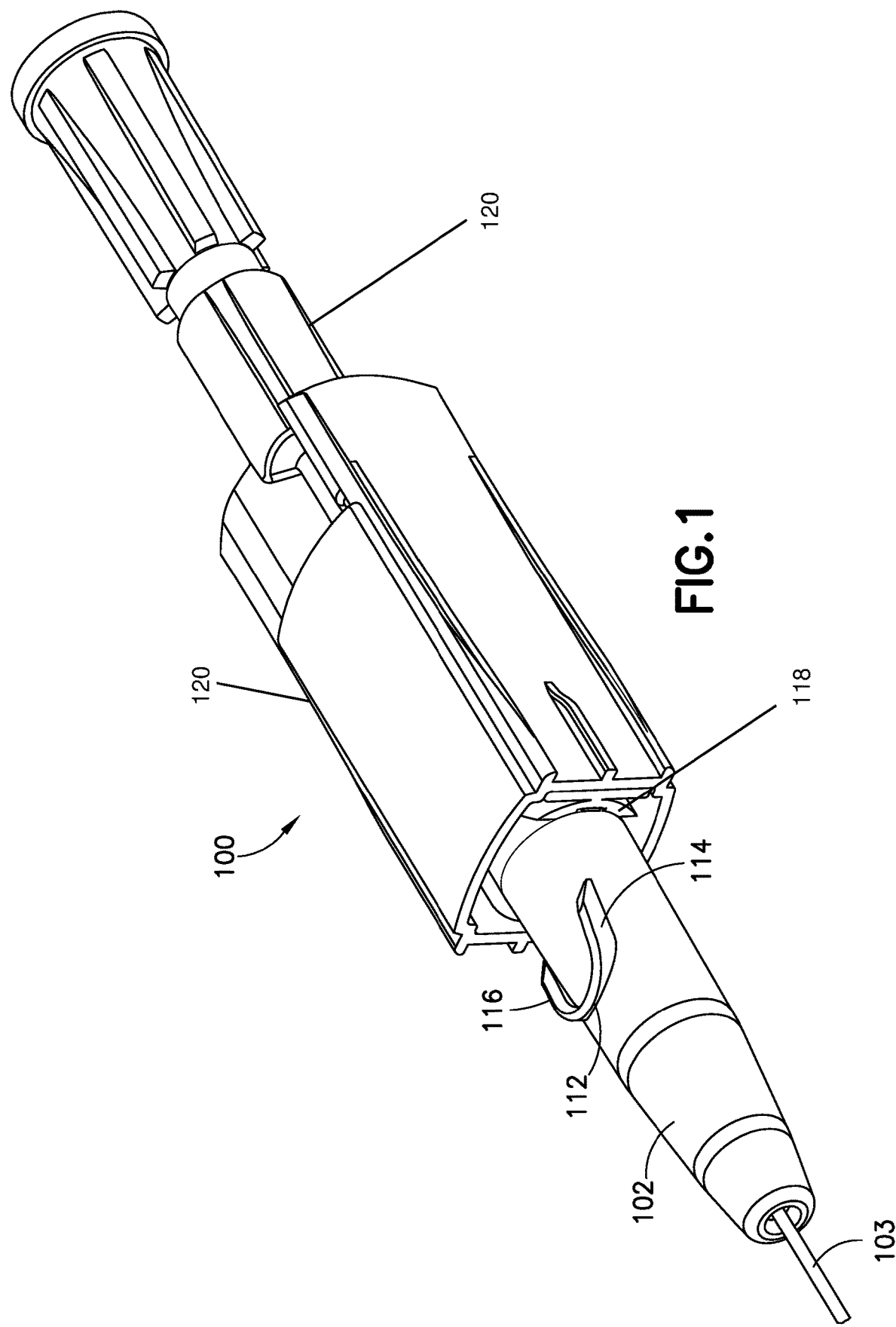
FIG. 1 illustrates a catheter hub incorporating an anti-rotation push tab.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Referring in more specific detail to FIG. 1 of the drawings, there is illustrated a medical device such as a safety IV catheter assembly 100 incorporating a catheter hub (hub) 102 and a flexible tube or cannula 103. The catheter hub 102 is releasably engaged to a needle tip shield 118 (housing). The catheter tube 103 is directly or indirectly connected to the hub 102 or housing 118. The material of the catheter tube 103 may consist of, for example, polyurethane (PU), FEP or PTFE (Teflon™). For purposes of illustration, the catheter hub 102 is shown attached to an introducer needle hub 120 prior to insertion. The catheter hub 102 includes a push tab 112 and anti-rotation features in the form of extension members 114 and 116. A user can engage the push tab 112 to advance the catheter hub 102 forward thereby advancing the catheter. As illustrated in FIG. 1, the push tab 112 extends radially from an upper surface of the catheter hub 102. The first extension 114 extends from a first side of the push tab 112 around the side of the upper surface of the catheter hub 102 and the second extension 116 extends from a second side of the push tab 112 around the other side of the upper surface of the catheter hub 102. The first extension 114 and the second extension 116 act as anti-rotation members that counteract rotation of the catheter hub 102. The push tab and first and second extensions together form a substantially C-shape when viewed from above.

The push tab and first and second extensions are shaped and configured to cradle a user's finger as the push tab 112 is advanced forward. The first extension 114 and second extension 116 resist angular rotation of the catheter hub 102 relative to the user's finger and enhance stability during insertion.

In an alternate embodiment (not shown), the push tab 112 and extension members 114, 116 are similarly disposed on a top distal surface of the needle tip shield 118, instead of on the catheter hub 102. The introducer needle hub 120 includes an opening at a top distal surface to allow the push tab 112 and extension members 114, 116 of the needle tip shield 118 to extend upwardly and be accessible to the user. The catheter tube 103 is directly or indirectly connected to the hub 102 or housing 118. Accordingly, the user can engage the push tab 112 on the needle tip shield 118 to advance the catheter hub 102 and catheter forward. After the catheter is inserted, the introducer needle hub 120 is used to withdrawn the introducer needle of the catheter assembly 100 from the catheter tube 103 and the catheter hub 102. Subsequently, a distal end of the introducer needle is retracted and enclosed in the needle tip shield 118. The push tab 112 and extension members 114, 116 of the needle tip shield 118 also aid the user to withdraw the introducer needle of the catheter assembly 100.

For this and other subsequently-described embodiments, all reference characters designating corresponding parts of the embodiments will be the same as in the embodiment of FIG. 1, except that they will be in a different series, for example, in the 200 series, or the 300 series. The differences of the second and third embodiments with respect to the first embodiment will now be described.

Figure 2:
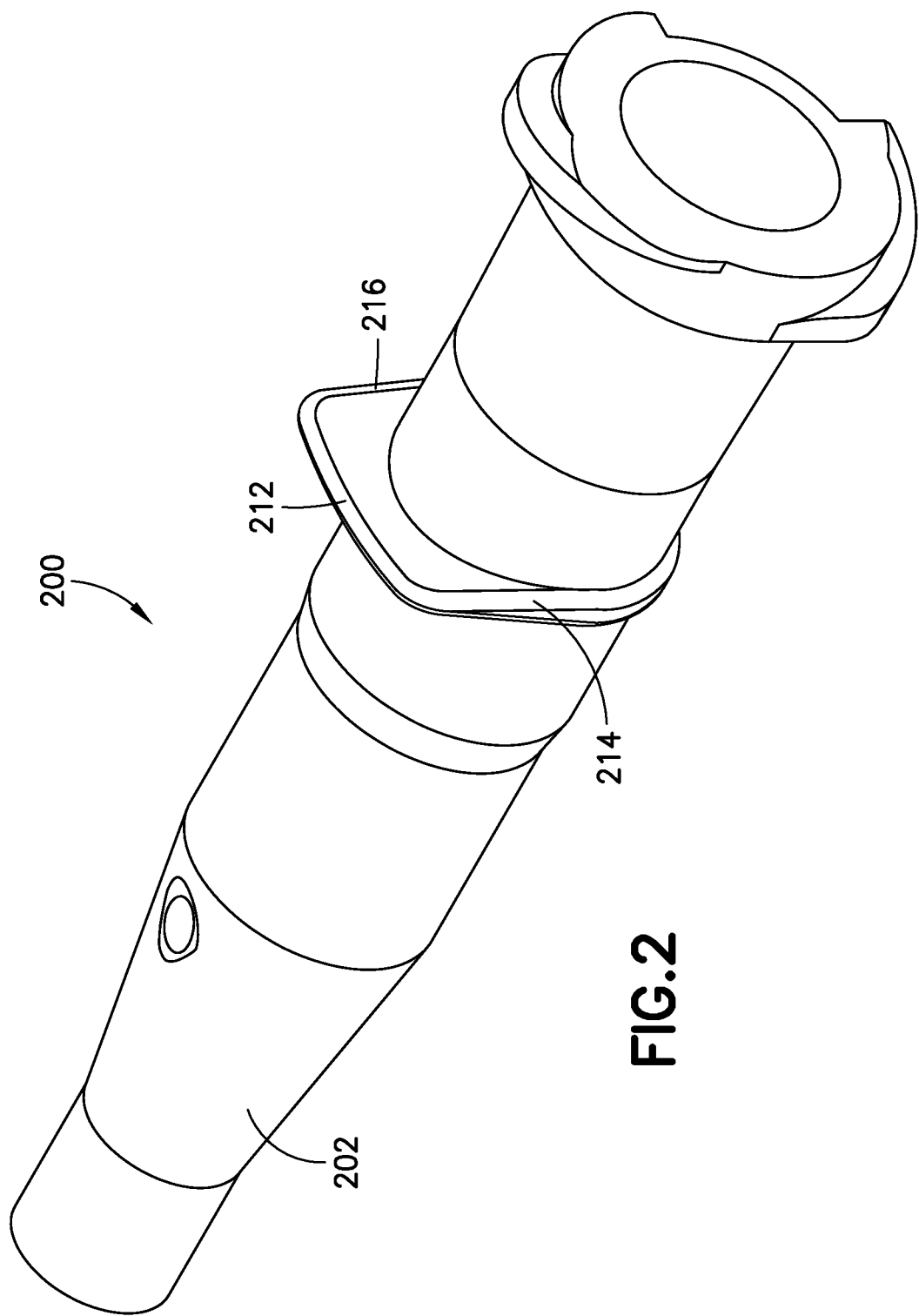
FIG. 2 illustrates a catheter hub incorporating a sculpted anti-rotation push tab.

FIG. 2 depicts a push tab 212 formed on an upper surface of a catheter hub 202 for a catheter hub 200. As illustrated in FIG. 2, the push tab 212 is a wall-like formation extending radially from an upper surface of the catheter hub 202. The push tab 212 includes a raised and sculpted configuration where a distal side of the wall-like main portion 212 is concave so as to conform to the curvature of the user's finger and allow the user to control rotation. A first extension 214 extends from a first side of the wall-like main portion 212 around an outer surface of the catheter hub 202, and a second extension 216 extends from a second side of the main portion 212 around the outer surface of the catheter hub 202. The first extension 214 and the second extension 216 act as anti-rotation members that counteract rotation of the catheter hub 202. The sculpted configuration of the push tab 212 provides a tactile feel for the user with regard to placement of the user's finger.

Figure 3:
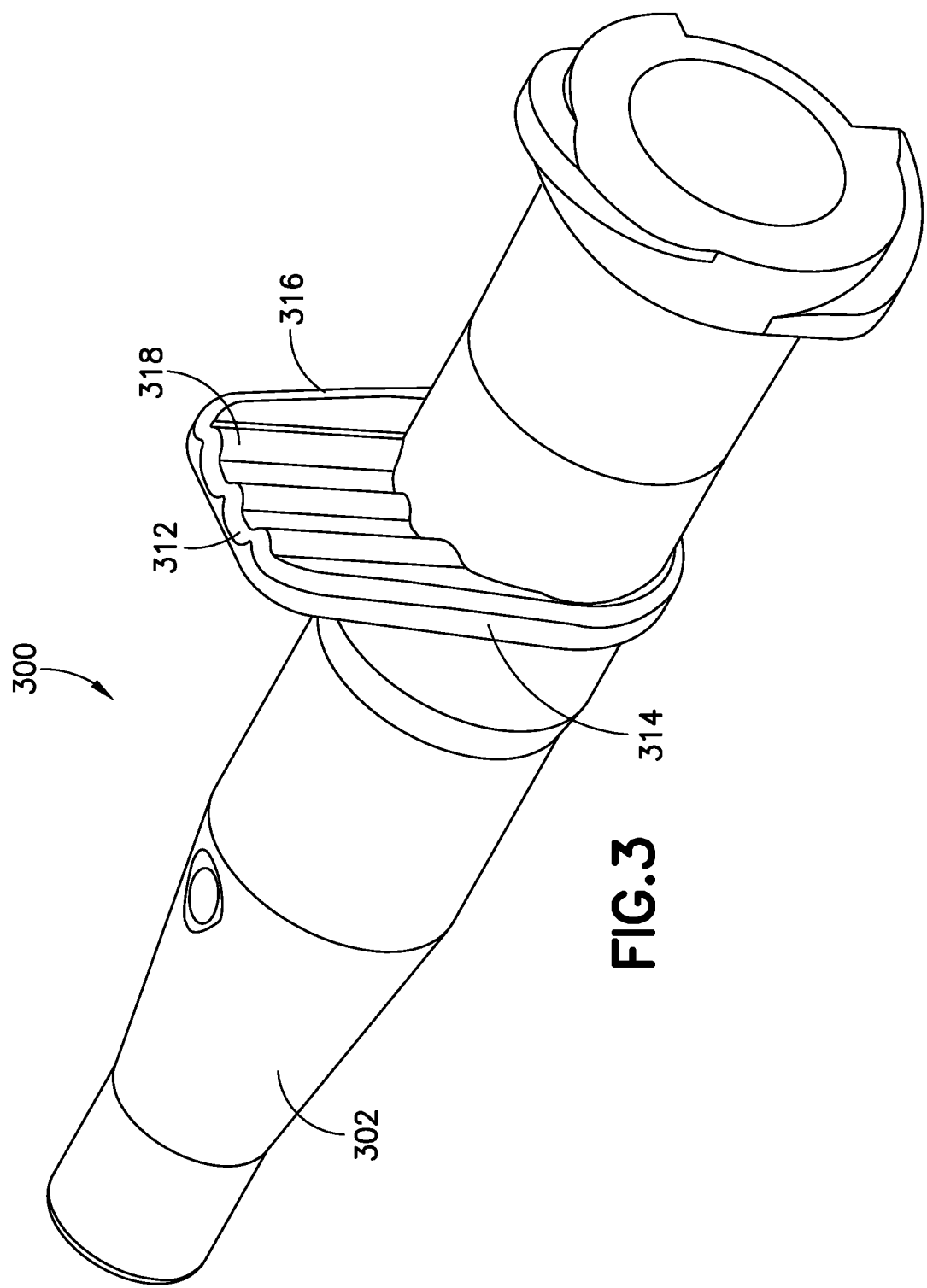
FIG. 3 illustrates a catheter hub incorporating a sculpted anti-rotation push tab including ribs.

FIG. 3 provides a sculpted push tab 312 on an upper surface of a catheter hub 302. The push tab 312 includes ribs 318 disposed on a wall-like main portion of the tab 312. Ribs 318 enhance the tactile feel with regard to placement of the user's finger and assist in maintaining the user's finger on the tab 310.

Figure 4:
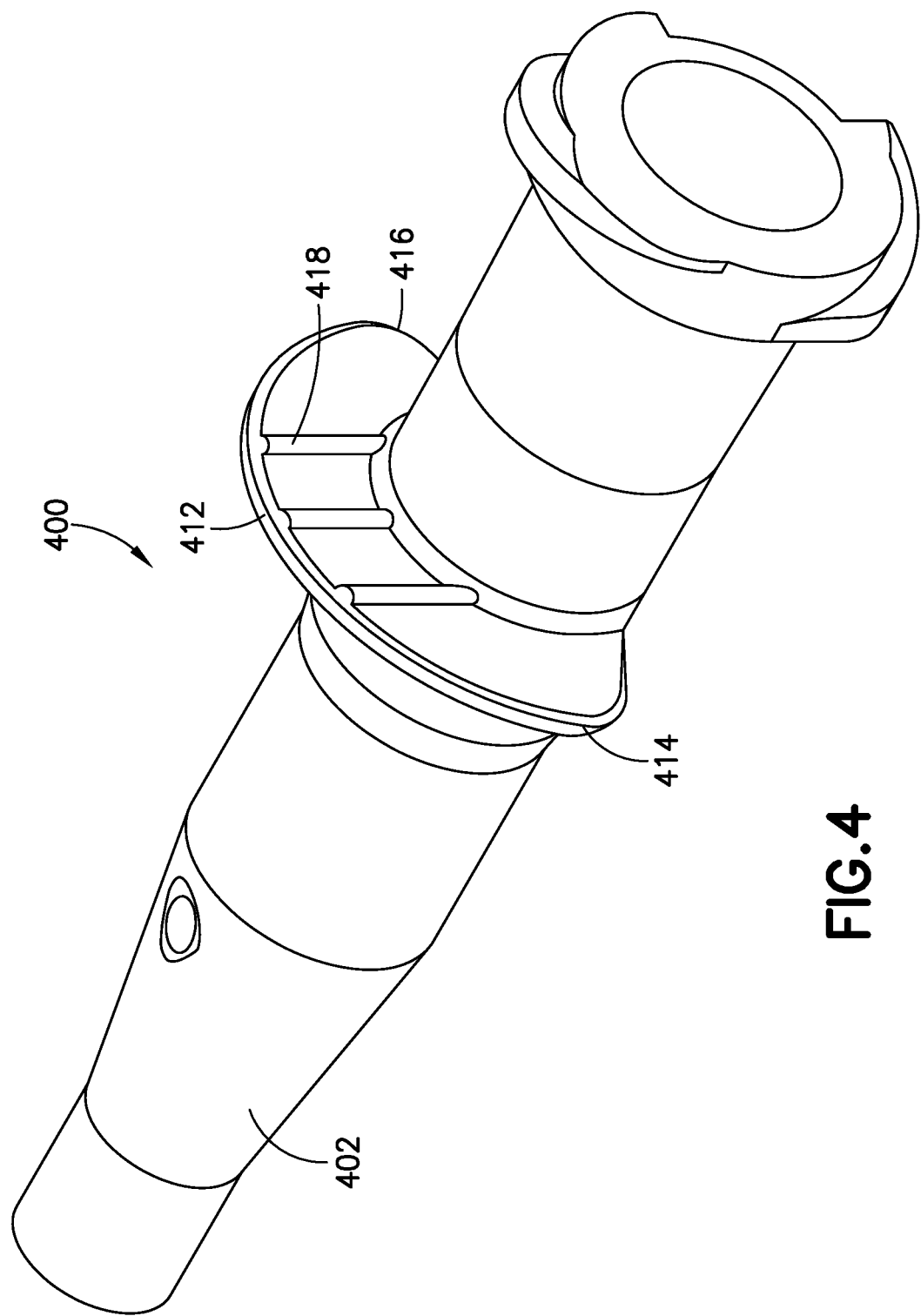
FIG. 4 illustrates a catheter hub incorporating an extended anti-rotation push tab.

A push tab 412 is formed on an upper surface of the catheter hub 402 illustrated in FIG. 4 for use with a catheter. The push tab 412 includes a wall-like main portion extending radially from an upper surface of the catheter hub 402. The push tab 412 also includes a first extension 414 and a second extension 416. The first extension 414 and second extension 416 both extend radially from side surfaces of the catheter hub. Together with the main portion 412, they provide a larger circumference for the finger-engaging surface than the embodiments of FIGS. 2 and 3. At least one rib 418 is formed on the push tab 412 to facilitate engagement with a user's finger and prevent rotation. The first and second extension 414 and 416 limit rotation of the catheter hub 402 such that as the catheter rotates either clockwise or counterclockwise, either the first extension 414 or the second extension 416 will contact the skin of the patient and prevent further rotation, while the push tab 412 is still in contact with the clinician's finger, allowing advancement.

Figure 5:
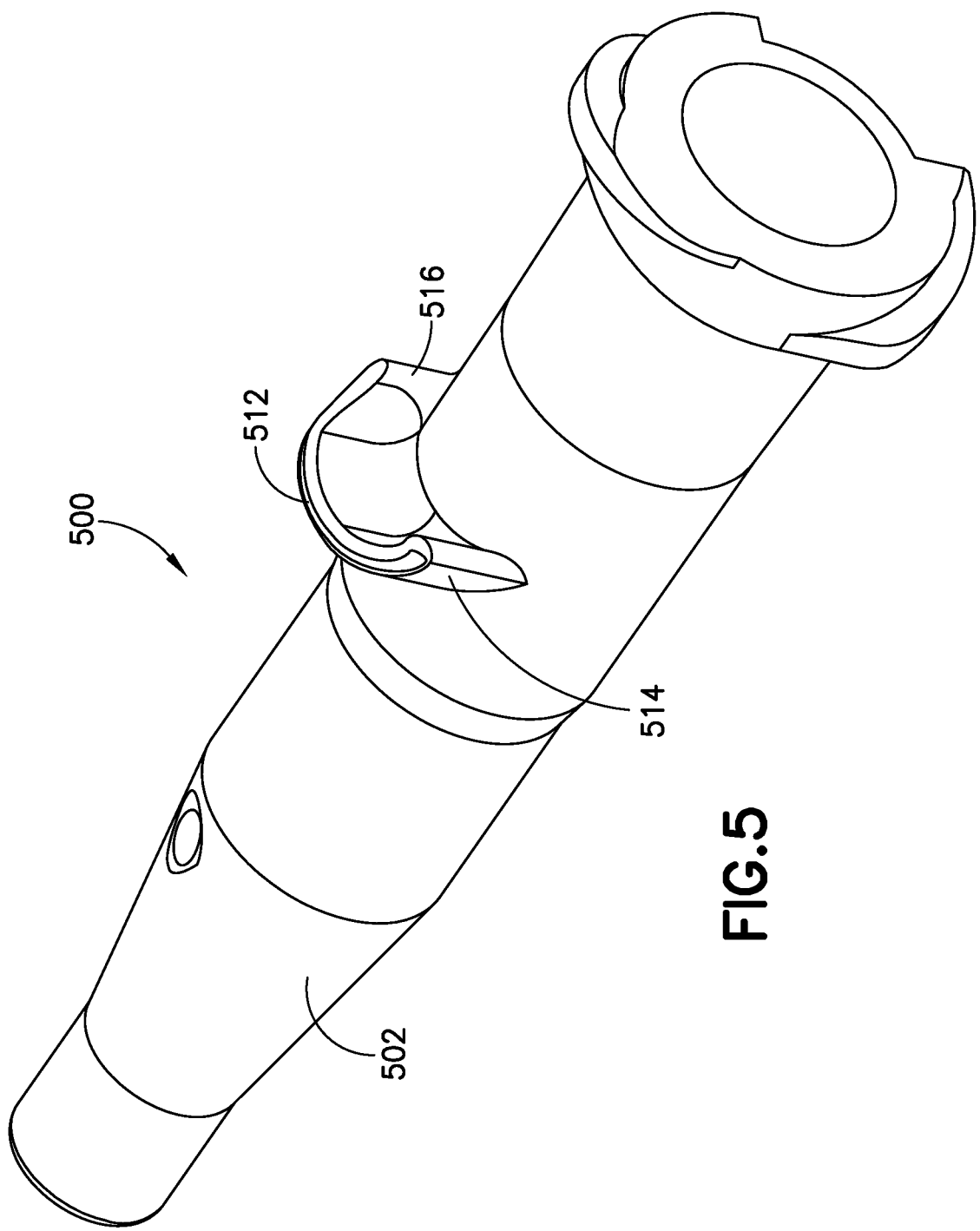
FIG. 5 illustrates a catheter hub incorporating a deep sculpted anti-rotation push tab.

FIG. 5 illustrates a catheter hub 502 with a more deeply sculpted push tab 512 formed on an upper surface of the catheter hub 502. The deep-sculpted push tab 512 includes a wall-like main portion extending radially from an upper surface of the catheter hub 502. A first extension 514 and a second extension 516 extend from the wall-like main portion of the push tab 512. The first extension 514 and second extension 516 both extend proximally on the catheter hub 502 and curve toward the main portion of the push tab 512 to cradle a user's finger by engaging the sides of the clinician's fingers and allow the user to control lateral motion and rotation. The first extension 514 and the second extension 516 act as anti-rotation members that counteract rotation of the catheter hub 502.

Figure 6:
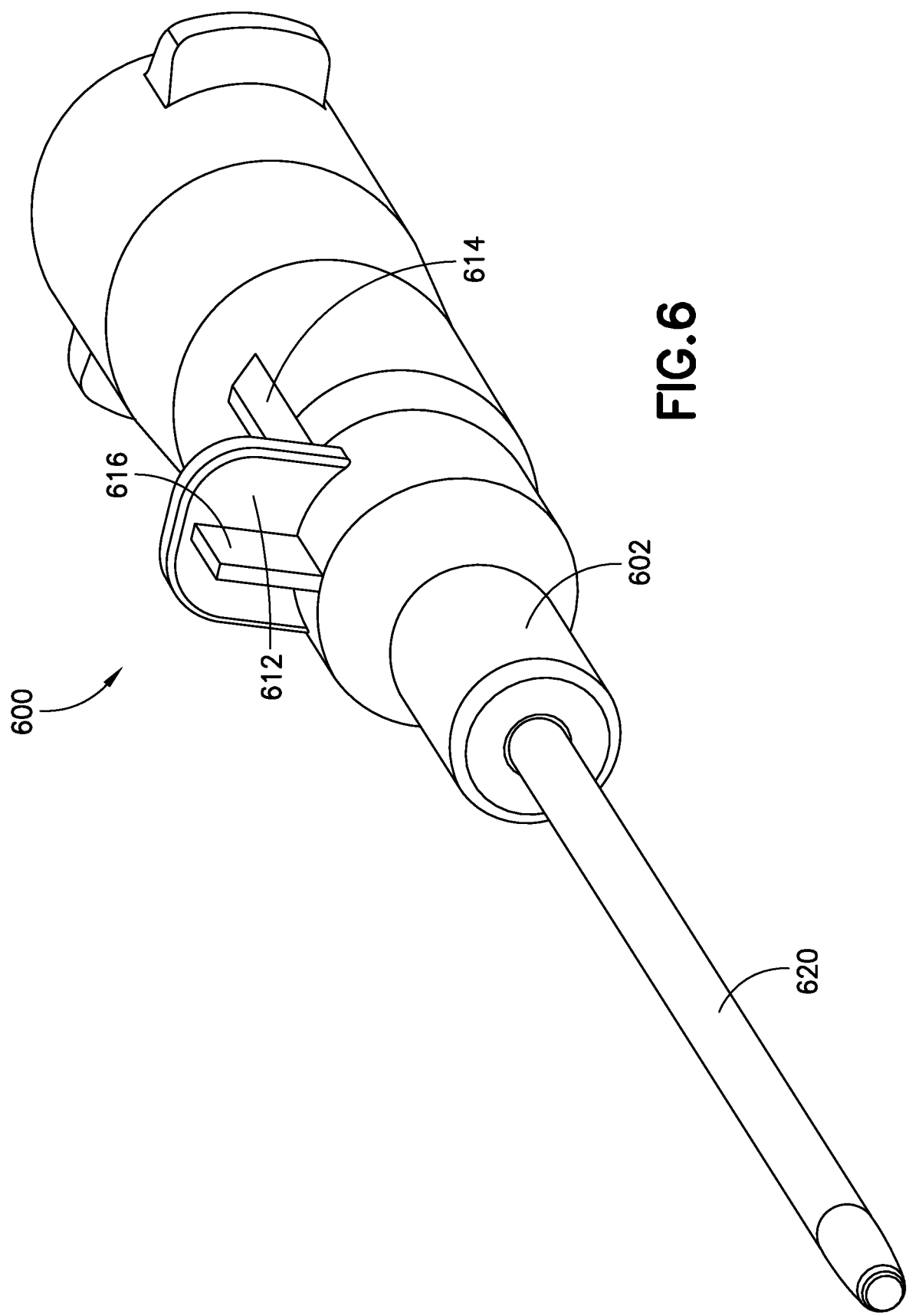
FIG. 6 illustrates a catheter hub incorporating an anti-rotation push tab according to another embodiment of the invention.

Regarding FIG. 6, a catheter hub 602 incorporating a catheter 620 is illustrated. A push tab 612 is formed on an upper surface of the catheter hub 602. As illustrated in FIG. 6, the push tab 612 is configured as a wall-like main portion extending radially from an upper surface of the catheter hub 602. A first cradling tab 614 extends from a first side of the push tab 612 perpendicular to a plane of the push tab 612. A second cradling tab 616 extends from a second side of the main portion 612 perpendicular to a plane of the push tab 612. The push tab 612, first extension 614 and second extension 616 thereby form a cradle shape to resist catheter hub rotation where the first extension 214 and the second extension 216 act as anti-rotation members that counteract rotation of the catheter hub 202.

Figure 7:
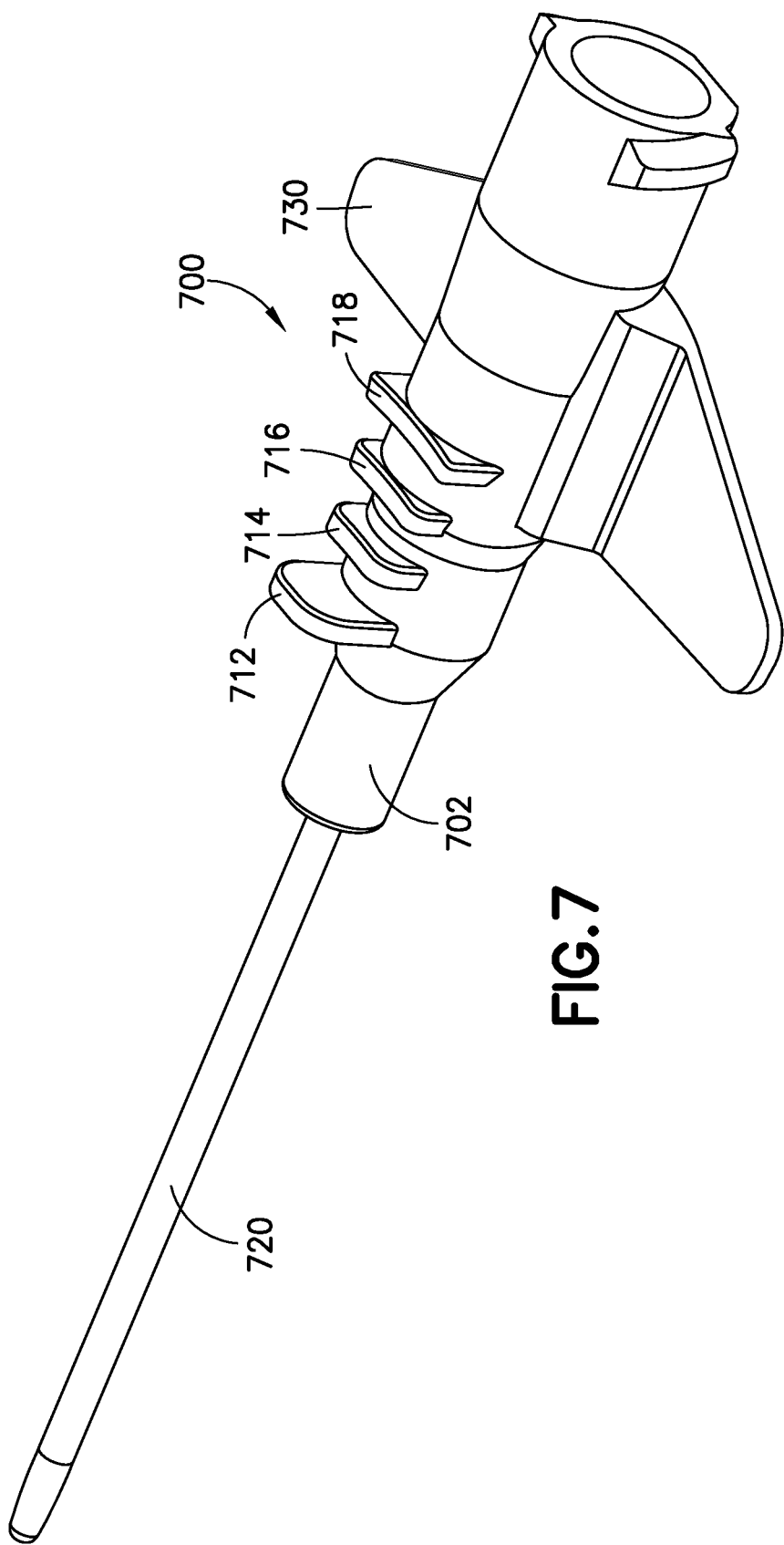
FIG. 7 illustrates a catheter hub incorporating an anti-rotation push tab according to still another embodiment of the invention.

FIG. 7 illustrates a wing catheter hub 702 incorporating a flexible IV catheter 720 and wings 730. An push tab 712 is formed on an upper surface of the catheter hub 702. As illustrated in FIG. 7, the push tab 712 includes a tall wall-like main portion extending radially from an upper surface of the catheter hub 702. Anti-rotation push tab 712 provides a cradling effect for the user's finger to aid insertion stability.

A first rib 714 parallel to the plane of the push tab 712, but shorter in height, extends from an upper surface of the catheter hub 702 and is spaced proximally from to the push tab 712. A second rib 716 and a third rib 718, also shorter in height than the first rib 714, may also extend from an upper surface of the catheter hub 702 parallel to the plane of the push tab 712. The ribs 714, 716, and 718 form a cradle shape to resist catheter hub rotation. Ribs 714, 716 and 718 also strengthen the catheter hub to prevent shrinkage which could cause leakage for any internal components of the catheter hub requiring a lengthwise seal.

Figure 8A:
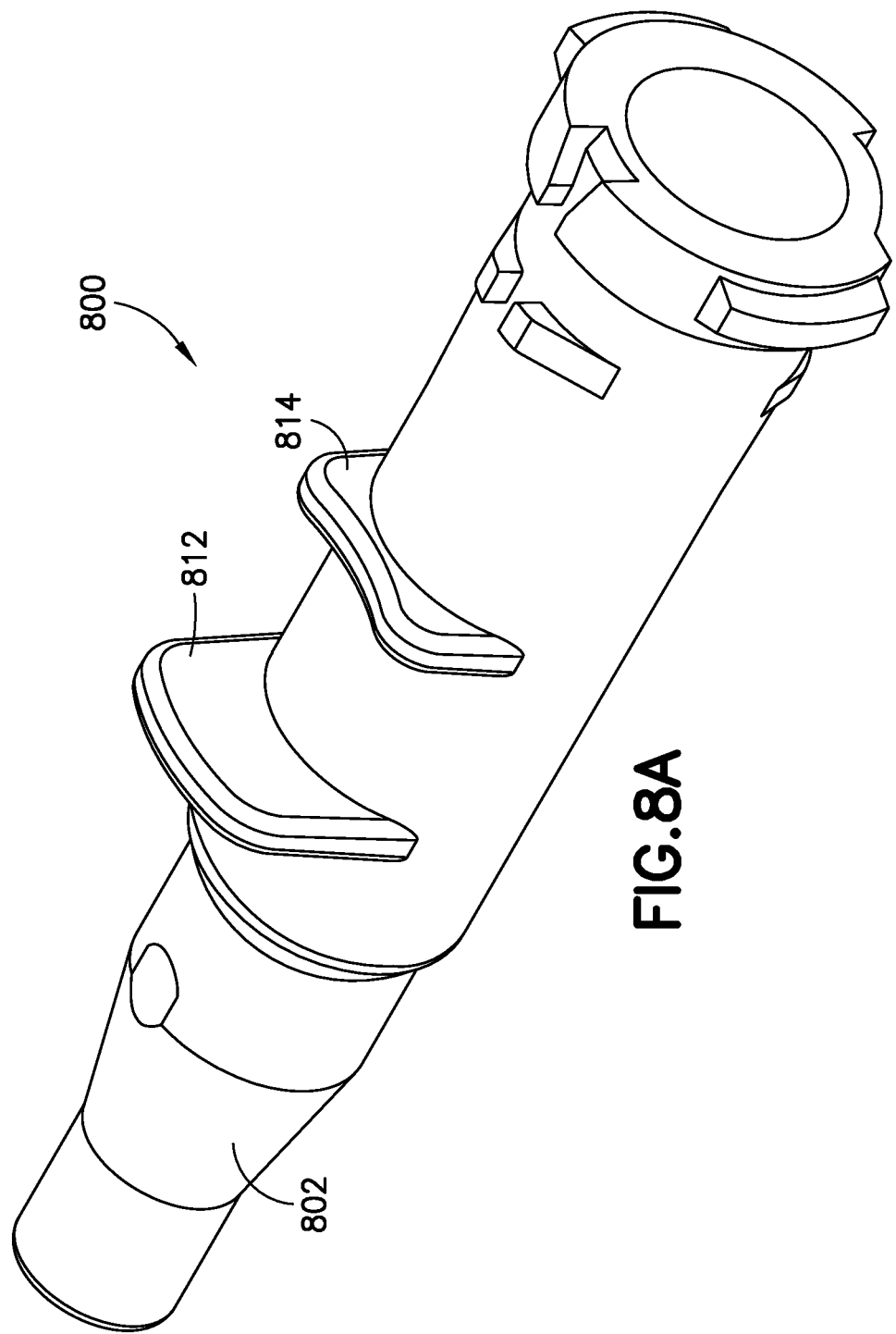
FIGS. 8A and 8B illustrate a catheter hub incorporating an anti-rotation push tab according to yet another embodiment of the invention.
Figure 8B:
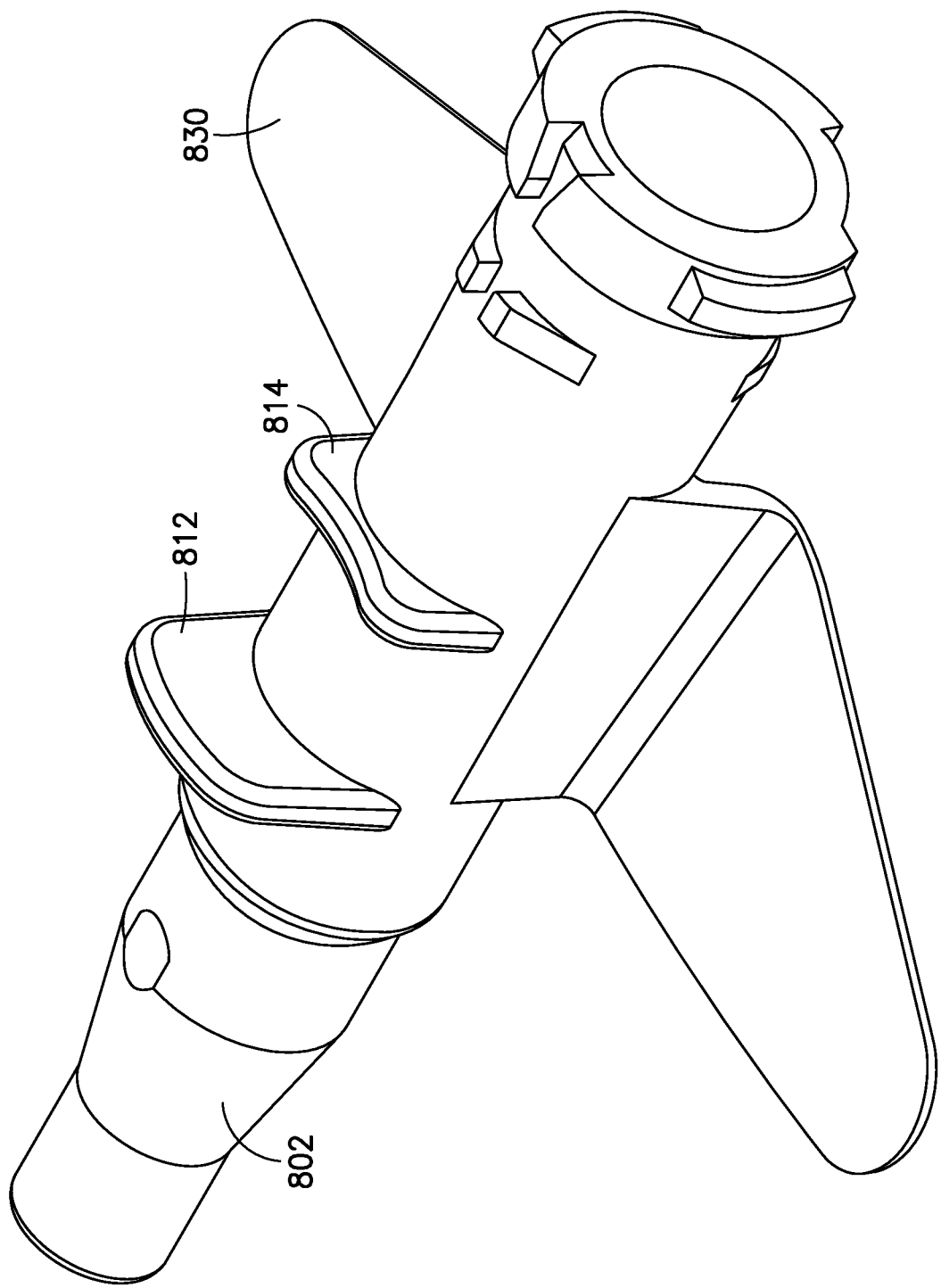

FIG. 7 illustrates three ribs 714, 716 and 718; however, a single rib 814 may be utilized to provide the necessary anti-rotational effect as illustrated in FIGS. 8A and 8B. The rib(s) 714, 716, 718 and 814 should be a distance from the push tab 712/812 where the rib is far enough from the push tab 712/812 to contact a user's advancing finger pad to provide stability but not so close that the finger pad does not contact the rib. The catheter hub 802 may be manufactured with or without wings 830 as shown in FIGS. 8B and 8A, respectively.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A medical device, comprising:
a hub or housing having:
 a push tab disposed on an upper surface of the hub or housing;
 a first tab extending from a first side of the push tab perpendicular to a plane of the push tab; and
 a second tab extending from a second side of the push tab and from the upper surface of the hub or housing in a direction perpendicular to the plane of the push tab and away from the push tab;
a cannula directly or indirectly connected to the hub or housing, wherein
the first tab and the second tab are substantially parallel;
the push tab includes a first side surface and a second side surface;
the first tab and the second tab extend between the first side surface and the second side surface; and
one of the first tab and the second tab includes an axial length and a radial height extending from the upper surface of the hub or housing, the axial length is greater than the radial height.

2. The medical device of claim 1, wherein the push tab extends radially in a vertical direction and perpendicular to a centerline of the medical device, the push tab extends from the upper surface of the hub or housing at a lower portion of the push tab, to an upper portion of the push tab.

3. The medical device of claim 1, wherein the first tab comprises a protrusion that extends radially from the upper surface of the hub or housing at a lower portion of the first tab, to a top surface of the first tab.

4. The medical device of claim 1, wherein the second tab comprises a protrusion that extends radially from the upper surface of the hub or housing at a lower portion of the second tab, to a top surface of the second tab.

5. The medical device of claim 1, wherein the first side of the push tab comprises a proximal side of the push tab.

6. The medical device of claim 1, wherein the second side of the push tab comprises a distal side of the push tab.

7. The medical device of claim 1, wherein the second tab extends radially over at least half of the push tab.

8. The medical device of claim 7, wherein the first tab radially extends less than the second tab of the push tab.

9. The medical device of claim 1, wherein the first tab extends axially parallel to a centerline of the hub or housing.

10. The medical device of claim 9, wherein the first tab extends on the upper surface of the hub or housing.

11. The medical device of claim 9, wherein an axial length of the first tab is greater than an axial length of the second tab.

12. The medical device of claim 1, wherein
the cannula comprises a catheter tube of a catheter; and
the hub or housing comprises a catheter hub of the catheter.

13. The medical device of claim 1, wherein
the cannula comprises a catheter tube of a safety catheter; and
the hub or housing comprises a tip shield for an introducer needle of the safety catheter.

14. The medical device of claim 1, wherein
an other of the first tab and the second tab includes an axial length and a radial height extending from the upper surface of the hub or housing, the radial height is greater than the axial length.

* * * * *